(12) United States Patent
Itoh

(10) Patent No.: US 7,158,606 B2
(45) Date of Patent: Jan. 2, 2007

(54) METHOD AND APPARATUS FOR DETECTING STATE OF BLOOD SAMPLE CONTAINED IN TEST TUBE, USING X RAYS

(75) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 0 days.

(21) Appl. No.: 11/325,356

(22) Filed: Jan. 5, 2006

(65) Prior Publication Data

US 2006/0159224 A1    Jul. 20, 2006

(30) Foreign Application Priority Data

Jan. 18, 2005    (JP)    ............... 2005-010820

(51) Int. Cl.
*G01N 23/04*    (2006.01)
(52) U.S. Cl. .......................................... 378/62; 378/66
(58) Field of Classification Search ................. 378/62, 378/64, 66, 68; 435/287.1; 436/63
See application file for complete search history.

(56) References Cited

U.S. PATENT DOCUMENTS

| 6,743,398 B1 * | 6/2004 | Itoh | ............................. 422/73 |
| 2005/0205788 A1 * | 9/2005 | Itoh | ............................. 250/343 |

FOREIGN PATENT DOCUMENTS

| JP | 2739928 | 1/1998 |
| JP | 2002-323479 | 11/2002 |

* cited by examiner

*Primary Examiner*—Courtney Thomas
(74) *Attorney, Agent, or Firm*—Nixon & Vanderhye P.C.

(57) ABSTRACT

A test tube having a plug and containing a blood sample is prepared. The blood sample is separated into blood serum and blood clot by a separation agent, and an air layer is interposed between the plug and the blood serum. The test tube is placed between an X-ray tube and an image pickup device. X rays are emitted from the X-ray tube to the test tube. An X-ray image corresponding to X rays passing through the test tube is picked up by the image pickup device, thereby detecting the internal state of the test tube.

7 Claims, 1 Drawing Sheet

METHOD AND APPARATUS FOR DETECTING STATE OF BLOOD SAMPLE CONTAINED IN TEST TUBE, USING X RAYS

CROSS-REFERENCE TO RELATED APPLICATIONS

This application is based upon and claims the benefit of priority from prior Japanese Patent Application No. 2005-010820, filed Jan. 18, 2005, the entire contents of which are incorporated herein by reference.

BACKGROUND OF THE INVENTION

1. Field of the Invention

The present invention relates to a method for detecting the state of a blood sample contained in a test tube, and a detection apparatus using this method.

2. Description of the Related Art

When a blood sample contained in a test tube is separated into blood serum and blood clot, using a centrifugal separator, the test tube contains a silicone separation agent to enable accurate separation. FIG. 2 shows a test tube 1 containing a silicone separation agent B. When the test tube 1 is used, blood serum A and blood clot C are separated from each other in the test tube 1 by the silicone separation agent B after a centrifugal separation process, as shown in FIG. 2. Further, an air layer D is defined between the blood serum A and a plug 2 that closes the opening of the test tube 1.

To extract, for example, only the blood serum A from the blood sample that is separated into the blood serum A and blood clot C, the extraction process is executed by sticking a nozzle through the plug 2 into the blood serum A. Before extracting the blood serum A, it is necessary to accurately detect the separation position of the blood sample in the test tube 1.

In other words, to position the tip of the nozzle at the bottom of the blood serum A, it is necessary to detect the boundary e between the air layer D and blood serum A, the boundary f between the blood serum A and silicone separation agent B, the boundary g between the blood clot C and silicone separation agent B, the top position a of the blood serum A, the top position b of the silicone separation agent B, the top position d of the air layer D, and the thickness h of the plug 2.

The top position a of the blood serum A, the top position b of the silicone separation agent B and the top position d of the air layer D all vary depending upon the amount of the blood clot C deposited on the bottom of the test tube 1. Accordingly, unless the top positions a, b and d are accurately detected, the tip of the nozzle, for example, may contact the silicone separation agent B to draw the agent B when the nozzle is inserted into the test tube 1 to draw the blood serum A. Further, the insertion of the nozzle may be stopped before the tip of the nozzle reaches the bottom of the blood serum A, failing in complete extraction of the blood serum A from the test tube 1.

Jpn. Pat. Appln. KOKAI Publication No. 2002-323479 discloses a determination apparatus for automatically determining, from the outside of a test tube, the separation position of blood serum and blood clot in the tube. This determination apparatus includes a holding member that holds, upright, a test tube with a blood sample contained therein, a detection coil provided around the test tube, and a signal supply unit for supplying a measurement signal of a predetermined frequency to the detection coil.

In the determination apparatus, the detection coil and test tube are moved relative to each other, with the measurement signal supplied from the signal supply unit to the detection coil. During the movement, the level of the measurement signal is significantly changed in accordance with the position of the detection coil. More specifically, the relative permeability of a silicone separation agent that separates blood serum from blood clot greatly differs from those of blood serum and clot. Accordingly, when the relative positions of the detection coil and test tube are changed and the detection coil reaches the position corresponding to the silicone separation agent, the level of the measurement signal supplied to the detection coil changes abruptly. By detecting the point at which the level of the measurement signal changes abruptly, the separation position of blood serum and clot is magnetically determined.

In medical facilities, such as hospitals, collected blood samples are contained in test tubes. Private information, such as blood-collection dates and hours, the names, sexes, ages, etc., of persons from whom blood is collected, is indicated by barcodes. The barcodes are printed on, for example, a barcode label 3 as shown in FIG. 2. The barcode label 3 is attached to the outer surface of the test tube 1 that contains blood.

In a conventional blood-collecting system employed in hospitals, the test tube 1 with the barcode label 3 attached thereto is carried to a blood collecting room, where information is read from the barcode label 3 and displayed on a display unit. Based on the read information, each person is called to the blood-collecting room, where blood is collected from them. This system is disclosed in, for example, Japanese Patent No. 2739928.

In the determination apparatus disclosed in the Japanese KOKAI Publication, the separation position of blood serum and clot can be detected. However, it is difficult to accurately determine, for example, the top position a of the blood serum A, the top position b of the silicone separation agent B, the top position d of the air layer D, and the thickness h of the plug 2. Further, the determination apparatus is inevitably complex in structure, which raises the equipment expenses.

In the prior art, in addition to the magnetic determination means utilizing the detection coil, detection means, which utilizes light, electromagnetic waves or air pressure, is known. However, both means have large detection errors, which means that, for example, neither the top position a of the blood serum A nor the top position b of the silicone separation agent B can be accurately detected. Moreover, when the barcode label 3 is attached to the test tube 1, this makes it difficult to accurately detect the separation position of the blood serum A and blood clot C.

BRIEF SUMMARY OF THE INVENTION

It is an object of the invention to provide a detection method that enables the state of a blood sample contained in a test tube to be accurately detected, and enables a detection apparatus to have a simple structure and be made at low cost, and also to provide the detection apparatus.

To attain the object, in accordance with an aspect of the invention, there is provided a detection method comprising:

preparing a test tube having a plug and containing a blood sample which is separated into blood serum and blood clot by a separation agent, an air layer being interposed between the plug and the blood serum;

placing the test tube between an X-ray tube and an image pickup device; and detecting an internal state of the test tube by emitting X rays from the X-ray tube to the test tube, and picking up an X-ray image corresponding to X rays passing through the test tube, using the image pickup device.

To attain the object, in accordance with an aspect of the invention, there is provided a detection apparatus comprising:

a test tube having a plug and containing a blood sample which is separated into blood serum and blood clot by a separation agent, an air layer being interposed between the plug and the blood serum;

a holding unit which holds the test tube upright;

an X-ray tube which emits X rays to the test tube from one side of the test tube;

an image pickup device which picks up an X-ray image corresponding to X rays passing through the test tube; and means for detecting an internal state of the test tube based on image data output from the image pickup device.

In the present invention, even if, for example, a barcode label is attached to the outer surface of a test tube, the internal state of the test tube, such as the position of blood serum, that of blood clot and that of an air layer, can be accurately detected. Further, unlike the prior art, the invention does not need such troublesome processes as detection of a measurement signal level, and determination of the separation position of the blood serum and blood clot based on the level. Accordingly, the structure of the detection apparatus can be simplified, thereby reducing the equipment cost.

Additional objects and advantages of the invention will be set forth in the description which follows, and in part will be obvious from the description, or may be leaned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Referring to the accompanying drawing, an embodiment of the invention will be described.

Figure 1:
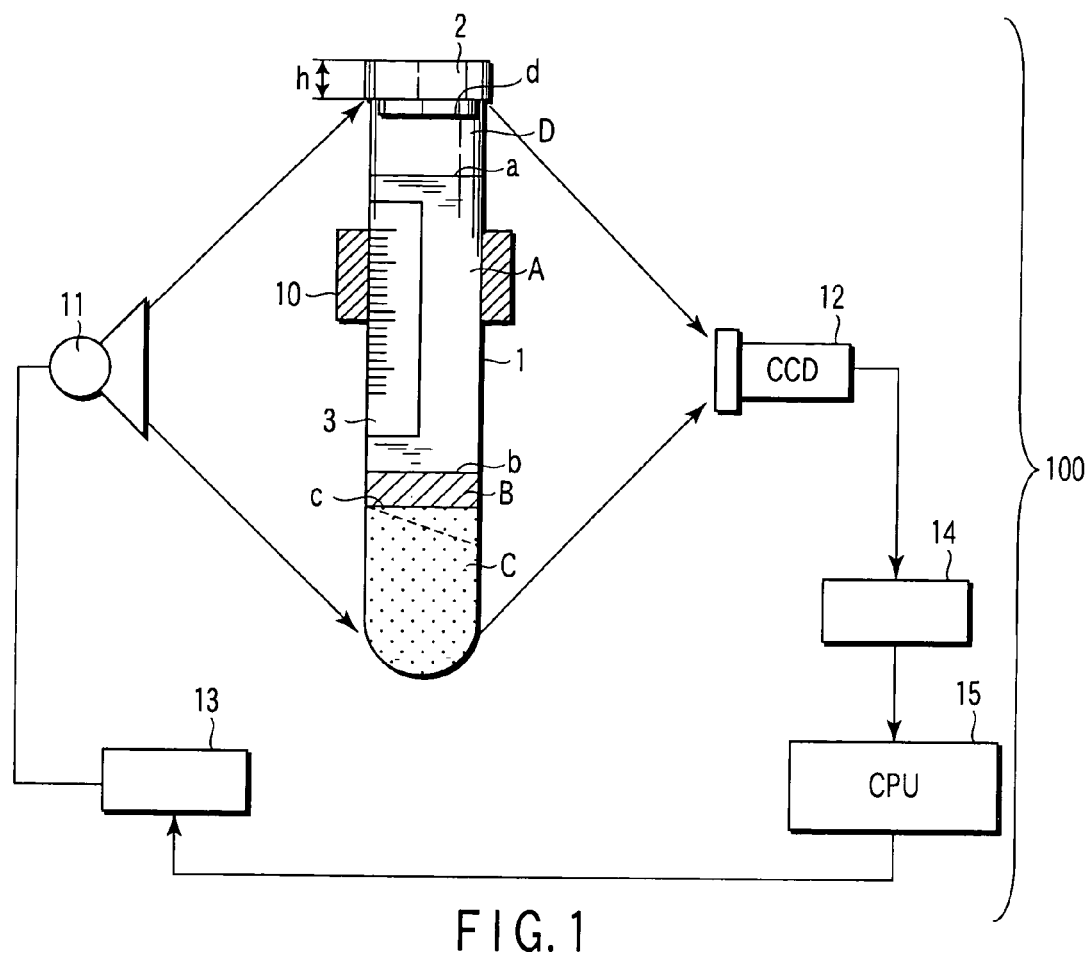
FIG. 1 is a diagram illustrating a detection apparatus according to an embodiment of the invention, which detects the state of a sample contained in a test tube, using X rays.
Figure 2:
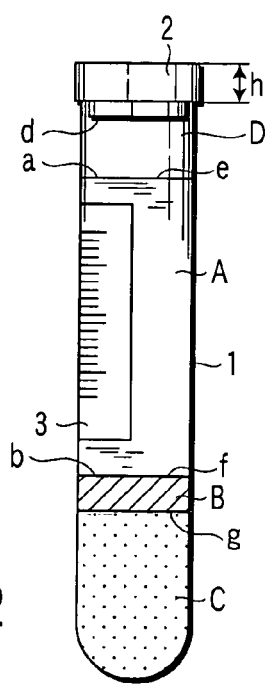
FIG. 2 is a side view of a conventional test tube containing a blood sample, illustrating a state in which blood serum and clot are separated from each other.

FIG. 1 shows a detection apparatus 100 according to the embodiment of the invention. The detection apparatus 100 uses X rays to detect the state of a sample contained in a test tube 1. The test tube 1 contains a blood sample and has its opening end closed by a plug 2, like the conventional test tube shown in FIG. 2. Further, a barcode label 3 indicating private information concerning the person, from whom blood is collected, is attached to the outer surface of the test tube 1.

Test tubes 1 include short-type ones and long-type ones. Short-type tubes have a length of 75 mm and a diameter of 13 mm. Long-type tubes have a length of 100 mm and a diameter of 16 mm. Each test tube 1 is held upright by a holding unit 10.

The blood sample in the test tube 1 is separated into blood serum A and blood clot C by, for example, a silicone separation agent B. The clot C is deposited on the bottom of the test tube 1. An air layer D is interposed between the blood serum A and the plug 2 closing the opening of the test tube 1.

As shown in FIG. 1, an X-ray tube 11 and a solid-state image pickup element 12, such as a CCD, are provided around the upright test tube 1. The X-ray tube 11 irradiates the entire test tube 1 with X rays from one side of the tube 1. The solid-state image pickup element 12 is an example of an image pickup device, and opposes the X-ray tube 11 with the test tube 1 interposed therebetween. The solid-state image pickup element 12 picks up an X-ray image acquired when X-rays have passed through the test tube 1. The X-ray tube 11 and solid-state image pickup element 12 are fixed in position.

The X-ray tube 11 is connected to a high-voltage generation unit 13. The solid-state image pickup element 12 is connected to a personal computer 15 via an image processing unit 14. Image data is output from the solid-state image pickup element 12 to the personal computer 15 and processed by it.

The X-ray tube 11 and solid-state image pickup element 12 form an X-ray television system. This enables various types of information indicating the internal state of the test tube 1 to be acquired at high speed and in real time. The various types of information include, for example, the top position a of the blood serum A, the top position b of the silicone separation agent B, the top position d of the air layer D, and the thickness h of the plug 2.

The test tube 1 with a blood sample contained therein is sent to, for example, a centrifugal separator, where the sample is separated into blood serum A and blood clot C. After that, the test tube 1 is placed between the X-ray tube 11 and solid-state image pickup element 12, kept upright by the holding unit 10.

When the high-voltage generation unit 13 applies a high voltage to the X-ray tube 11, the X-ray tube 11 emits X rays to the entire test tube 1. The X rays emitted to the test tube 1 pass through the plug 2, barcode label 3, and the blood serum A, silicone separation agent B, blood clot C and air layer D in the test tube 1. The solid-state image pickup element 12 receives the X rays passing through the test tube 1, thereby picking up an X-ray image.

Image data is output from the solid-state image pickup element 12 to the personal computer 15 via the image processing unit 14. As a result, an image containing various types of data that indicate the internal state of the test tube 1 is displayed. The various types of data include, for example, the thickness h of the plug 2, the top position d of the air layer D, the top position a of the blood serum A, the top position b of the silicone separation agent B and the top position c of the blood clot C.

Thus, even if the barcode label 3 covers the blood serum A in the test tube 1 from the outside of the tube, the internal state of the test tube 1 can be detected by the X rays that pass through the barcode label 3. More specifically, even if the silicone separation agent B is inclined in the test tube 1 as indicated by the broken line of FIG. 1, this can be accurately detected in the X-ray image picked up by the solid-state image pickup element 12. Similarly, even if the upper portion of the silicone separation agent B is mixed with the blood serum A, or the lower portion of the silicone separation agent B is mixed with the blood clot C, and hence the separation state of the blood serum A and blood clot C is ambiguous, this can be accurately detected in the X-ray image picked up by the solid-state image pickup element 12.

Furthermore, the above-described structure can omit troublesome processes required in the prior art, such as detection of a measurement signal level, and determination of the separation position of the blood serum A and blood clot C based on the level. Accordingly, the structure of the detection apparatus 100 can be simplified, thereby reducing the equipment cost.

In the above-described embodiment, the X-ray tube 11 for emitting X rays to the test tube 1 and the solid-state image pickup element 12 for picking up an X-ray image are fixed opposing each other, with the test tube 1 interposed therebetween. However, the invention is not limited to this structure. For instance, the X-ray tube 11 and solid-state image pickup element 12 may be movable at a constant speed in the height direction of the test tube 1. Alternatively, the test tube 1 may be vertically movable at a constant speed, with the X-ray tube 11 and solid-state image pickup element 12 fixed. In any case, the internal state of the test tube 1 ranging from the plug 2 to the position of the silicone separation agent B can be detected using X rays.

In addition, the image pickup device is not limited to the solid-state image pickup element 12. For instance, an X-ray television system that incorporates a television camera having an image intensifier may be used as the image pickup device for displaying an X-ray image.

The detection apparatus of the invention can be combined with a conveyance apparatus (e.g., a belt conveyor) for conveying a test tube with a blood sample contained therein. Specifically, the detection apparatus and a robot arm may be provided across the middle portion of the conveyance apparatus, to enable a test tube to be transferred to the holding unit of the detection apparatus by the robot arm when the test tube is conveyed to the position corresponding to the detection apparatus. X rays are emitted to the test tube when the test tube is held upright by the holding unit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A detection method comprising:
   preparing a test tube having a plug and containing a blood sample which is separated into blood serum and blood clot by a separation agent, an air layer being interposed between the plug and the blood serum;
   placing the test tube between an X-ray tube and an image pickup device; and
   detecting an internal state of the test tube by emitting X rays from the X-ray tube to the test tube, and picking up an X-ray image corresponding to X rays passing through the test tube, using the image pickup device.

2. The detection method according to claim 1, wherein the internal state of the test tube is at least one of a thickness of the plug, a position of the blood serum, a position of the separation agent and a position of the blood clot.

3. The detection method according to claim 1, wherein the image pickup device is a solid-state image pickup element.

4. A detection apparatus comprising:
   a test tube having a plug and containing a blood sample which is separated into blood serum and blood clot by a separation agent, an air layer being interposed between the plug and the blood serum;
   a holding unit which holds the test tube upright;
   an X-ray tube which emits X rays to the test tube from one side of the test tube;
   an image pickup device which picks up an X-ray image corresponding to X rays passing through the test tube; and
   means for detecting an internal state of the test tube based on image data output from the image pickup device.

5. The detection apparatus according to claim 4, wherein the image pickup device is a solid-state image pickup element.

6. The detection apparatus according to claim 4, wherein the X-ray tube opposes the image pickup device, with the test tube interposed therebetween.

7. The detection apparatus according to claim 4, further comprising a label attached to an outer surface of the test tube.

* * * * *